US00PP14124P39

(12) United States Plant Patent
Lowe

(10) Patent No.: US PP14,124 P3
(45) Date of Patent: Sep. 2, 2003

(54) GERANIUM PLANT NAMED 'CAROL'

(75) Inventor: Carl Lowe, New Port (GB)

(73) Assignee: Future Plants V.O.F., Lisserbroek (NL)

( * ) Notice: Subject to any disclaimer, the term of this patent is extended or adjusted under 35 U.S.C. 154(b) by 37 days.

(21) Appl. No.: 09/887,109

(22) Filed: Jun. 25, 2001

(65) Prior Publication Data

US 2002/0199229 P1 Dec. 26, 2002

(51) Int. Cl.[7] ..... A01H 5/00

(52) U.S. Cl. ..... Plt./324

(58) Field of Search ..... Plt./324

*Primary Examiner*—Bruce R. Campell
*Assistant Examiner*—Anne Marie Grünberg
(74) *Attorney, Agent, or Firm*—C. A. Whealy

(57) ABSTRACT

A distinct cultivar of Geranium plant named 'Carol', characterized by its compact plant habit; numerous purple-colored flowers; and long flowering period.

2 Drawing Sheets

BACKGROUND OF THE INVENTION

The present Invention relates to a new and distinct cultivar of Geranium plant, botanically known as *Geranium cinereum,* and hereinafter referred to by the cultivar name Carol.

The new Geranium originated from a cross-pollination of two unidentified selections of *Geranium cinereum,* not patented. The new Geranium was discovered by the Inventor in 1994 in Newport, England. Plants of the new Geranium differ primarily from plants of the unidentified parental selections in flower color.

Asexual reproduction of the new cultivar by divisions in Newport, England since 1997, has shown that the unique features of this new Geranium are stable and reproduced true to type in successive generations.

SUMMARY OF THE INVENTION

Plants of the cultivar Carol have not been observed under all possible environmental and cultural conditions. The phenotype may vary somewhat with variations in environment such as temperature, light intensity, daylength, irrigation amount and frequency, and/or fertilizer rate without, however, any variance in genotype.

The following traits have been repeatedly observed and are determined to be the unique characteristics of 'Carol'. These characteristics in combination distinguish 'Carol' as a new and distinct cultivar:

1. Compact plant habit.
2. Numerous purple-colored flowers.
3. Long flowering period.

In side-by-side comparisons conducted by the Inventor in Newport, England, plants of the new Geranium are more floriferous and flower for a longer period of time than plants of the *Geranium cinereum* cultivar Ballerina, not patented. In addition, plants of the new Geranium have purple-colored flowers whereas plants of the cultivar Ballerina have light pink-colored flowers.

In side-by-side comparisons conducted by the Inventor in Newport, England, plants of the new Geranium are more compact and have smaller flowers than plants of an unidentified selection of *Geranium psilostemon,* not patented.

BRIEF DESCRIPTION OF THE PHOTOGRAPHS

The accompanying colored photographs illustrate the overall appearance of the new Geranium, showing the colors as true as it is reasonably possible to obtain in colored reproductions of this type. Colors in the photographs may differ slightly from the color values cited in the detailed botanical description which accurately describe the colors of the new Geranium.

The photograph on the first sheet comprises a side perspective view of a typical one-year old flowering plant of 'Carol' grown in the outdoor landscape.

The photograph at the top of the second sheet is a close-up view of a typical open flower of 'Carol'.

The photograph at the bottom of the second sheet is a close-up view of typical leaves of 'Carol'.

DETAILED BOTANICAL DESCRIPTION

In the following description, color references are made to The Royal Horticultural Society Colour Chart except where general terms of ordinary dictionary significance are used. Plants used for the following description were about one year old and grown under outdoor field conditions which closely approximate commercial production conditions during the spring and summer in Lisserbroek, The Netherlands.

Botanical classification: *Geranium cinereum* cultivar Carol.
Parentage: Cross-pollination of two unidentified selections of *Geranium cinereum,* not patented.
Propagation:
- *Type cutting.*—By divisions.
- *Time to initiate roots.*—About 20 days at 18° C.
- *Root description.*—Thick, somewhat fleshy, brown in color.

Plant description:
- *Form.*—Perennial flowering plant; spreading, mounded and prostrate growth habit. Compact plant habit; appropriate for 1.7 to 2-liter containers.

*Crop time.*—After rooting, about 20 to 30 weeks are required to produce finished flowering plants in 17-cm containers.

*Plant height.*—About 10 to 15 cm.

*Plant diameter.*—About 25 cm.

*Vigor.*—Moderately vigorous.

*Lateral branch description.*—Number per plant: About 4. Length: About 12 cm. Diameter: About 2.5 mm. Internode length: About 4 cm. Texture, upper and lower surfaces: Densely tomentose. Color: Upper surface: 178A to 176A. Lower surface: 144A.

*Stipule description.*—Quantity: Two stipules per internode. Length: About 4 mm. Width: About 2 mm. Shape: Lanceolate. Texture: Pubescent. Color: 137A to 137B.

*Foliage description.*—Leaves opposite, simple, generally symmetrical, and long-persisting. Quantity per lateral branch: About 6. Length: About 3 cm. Width: About 3 cm. Shape: Palmately lobed. Apex: Acute. Base: Sagittate. Margin: Deeply serrate to incised. Texture, upper and lower surfaces: Densely tomentose; hairs short, less than 0.1 mm in length. Venation pattern: Palmate. Petiole: Length: About 3 to 5 cm. Diameter: About 1 mm. Color: Young foliage, upper surface: 137A. Young foliage, lower surface: 138A to 138B. Mature foliage, upper surface: 137A. Mature foliage, lower surface: 138A. Venation, upper surface: 137A. Venation, lower surface: 138A. Petiole: 143A to 143B.

Flower description:

*Appearance.*—Single rounded cupped to almost flat flowers with five petals with usually two per lateral stem. Flowers not persistent.

*Quantity of flowers.*—About 10 flowers per lateral stem.

*Natural flowering season.*—Long flowering period, summer through fall in the Netherlands; flowering continuous.

*Fragrance.*—None detected.

*Flower longevity.*—About 4 days.

*Flower size.*—Depth: About 8 mm. Diameter: About 3 cm.

*Flower buds* (*about five days before opening*).—Length: About 6 mm. Diameter: About 5 mm. Shape: Ovoid. Color: 141A.

*Petals.*—Length: About 1.8 cm. Width: About 1.4 cm. Shape: Broadly obovate. Apex: Rounded to retuse. Base: Attenuate. Margin: Entire. Texture: Somewhat rugose; dull. Color: When opening, upper surface: 78A. When opening, lower surface: 78B. Fully opened, upper surface: 74B to 78A; interveinal areas towards petal base, close to 155D; veins and base, close to 79A. Fully opened, lower surface: 74B to 78B.

*Sepals.*—Quantity: Five. Calyx height: About 6 mm. Calyx diameter (widest point): About 1.5 cm. Calyx shape: Rotate, slightly cupped. Sepal shape: Ovate to elliptic; apex, mucronate; margin, entire. Texture: Upper surface: Smooth. Lower surface and margins: Densely tomentose. Color: Upper surface: 141B. Lower surface: 141A.

*Peduncle.*—Length: About 2.8 cm. Angle: Erect to about 25° from vertical. Strength: Strong. Color: 144A.

*Reproductive organs.*—Stamens: Quantity: Ten. Anther shape: Reniform; dorsifixed. Anther length: About 2 mm. Anther color: Close to 202A. Pollen amount: Moderate. Pollen color: Green brown. Pistils: Quantity: Ten. Pistil length: About 3.5 mm. Style length: About 3.2 mm. Style color: Close to 71B. Stigma color: 71B. Ovary color: 144C to 145A.

*Seed description.*—Seed development has not been observed.

Disease resistance: Plants of the new Geranium have not been noted to be resistant to pathogens common to Geranium.

Temperature tolerance: Plants of the new Geranium are tolerant to temperatures from 15 to 40° C.

It is claimed:

1. A new and distinct cultivar of Geranium plant named 'Carol', as illustrated and described.

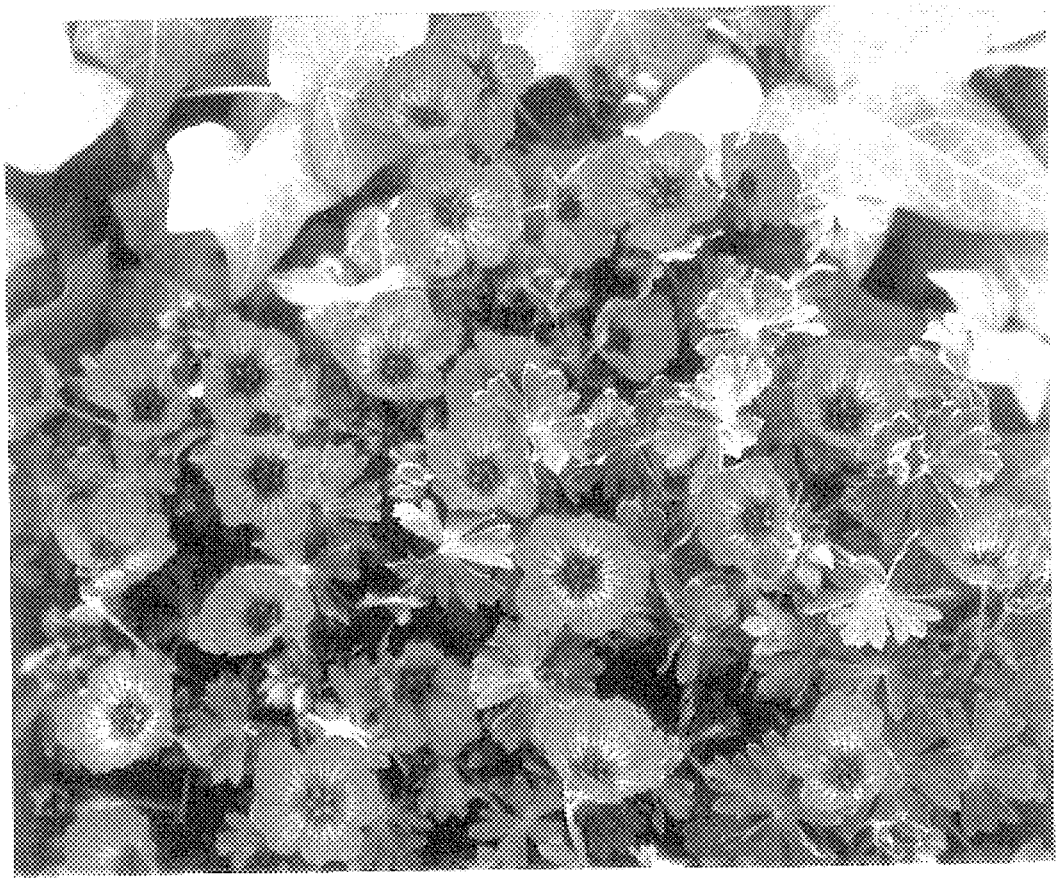

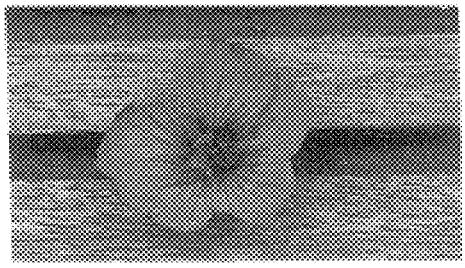
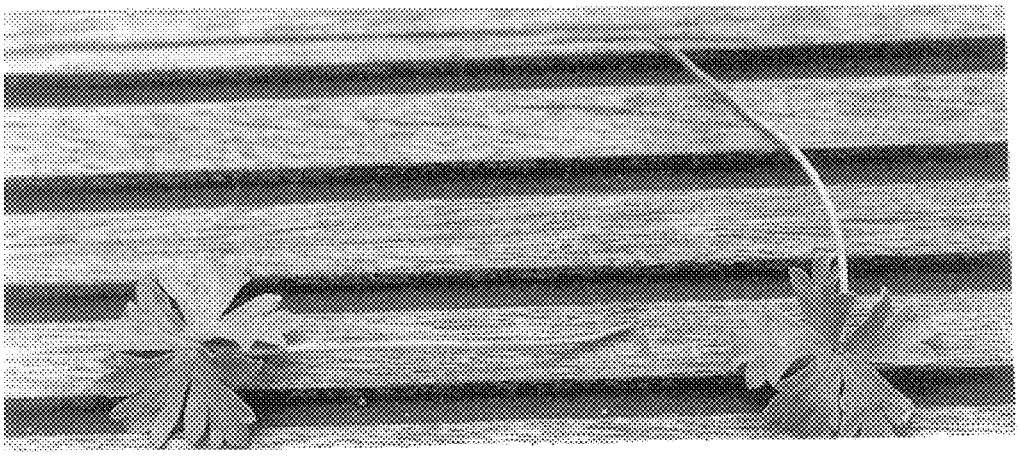

* * * * *